United States Patent [19]
Sharpe et al.

[11] Patent Number: 5,310,406
[45] Date of Patent: May 10, 1994

[54] ENDOSCOPIC ASPIRATOR SURGICAL INSTRUMENT

[75] Inventors: Leslie A. Sharpe, Edina, Minn.; Francis C. Peterson, Prescott, Wis.

[73] Assignee: Sharpe Endosurgical Corporation, Minneapolis, Minn.

[21] Appl. No.: 880,954

[22] Filed: May 8, 1992

[51] Int. Cl.$^5$ .............................................. A61M 3/00
[52] U.S. Cl. ................................... 604/35; 604/702; 126/4
[58] Field of Search .................. 604/902, 22, 35, 36, 604/264, 27, 35, 902; 126/4

[56] References Cited

U.S. PATENT DOCUMENTS

| | | | |
|---|---|---|---|
| Re. 33,258 | 7/1990 | Onik et al. | |
| 2,012,363 | 8/1935 | Vogel | 604/22 |
| 3,776,238 | 12/1973 | Peyman et al. | |
| 3,835,842 | 9/1974 | Iglesias | |
| 3,870,048 | 3/1975 | Yoon | |
| 3,882,854 | 5/1975 | Hulka et al. | |
| 4,393,872 | 7/1983 | Reznik et al. | 604/22 X |
| 4,445,517 | 5/1984 | Feild | 604/35 X |
| 4,610,664 | 9/1986 | Harle | 604/902 X |
| 4,644,951 | 2/1987 | Bays | 604/22 X |
| 4,662,371 | 5/1987 | Whipple et al. | 604/702 X |
| 4,958,621 | 9/1990 | Topel et al. | |
| 5,151,094 | 9/1992 | Hanfli | 604/902 |

OTHER PUBLICATIONS

"Innovation Sports Announces The K.M.D. Post-OP Brace, A Marriage of Cost and Control," Physical Therapy Products, Jan. 1992.
"The 'S-1' Support, The Lumbar Stabilizer," IEM Orthopaedic Systems, Inc., Ravenna, Ohio.
Ultraflex Dynamic Splint System, Bio-Tech, Inc., Malvern, Pa.
VersaWrist, Smith & Nephew DonJoy, Inc., Carlsbad, Calif.
"New Lightweight Knee Brace For Global Instabilities Of The Knee", Smith & Nephew DonJoy, Inc., Carlsbad, Calif.
Ultraflex Dynamic Splint, Bio-Tec, Inc., Malvern, Pa.
17B70 Otto Bock System Positioning Joint, Otto Bock, Orthopedic Industry, Inc., Minneapolis, Minn.
Knee ROM Splints from LMB, LMB Hand Rehab Products, Inc., San Luis Obispo, Calif.
Pacesetter Post-Op Knee Brace by Carapace Incorporated of Tulsa, Okla., a Lohmann Company.
Cooke ® Surgical, Endoscopic Curved Needle Driver Sets and Components.
Cook Urological ® Incorporated, Endoscopic Introducer/Extractor.
*Official Gazette,* General and Mechanical, Mar. 24, 1992, Locking Dilator for Peel Away Introducer Sheath, p. 2233.

*Primary Examiner*—Richard J. Apley
*Assistant Examiner*—Beverly A. Meindl
*Attorney, Agent, or Firm*—Merchant, Gould, Smith, Edell, Welter & Schmidt

[57] ABSTRACT

An aspiration device for laparoscopic surgery has a tube with a proximal end. A tool access port concentric with the tube permits insertion of a grasping tool for holding a sponge at the distal end of the tube.

5 Claims, 5 Drawing Sheets

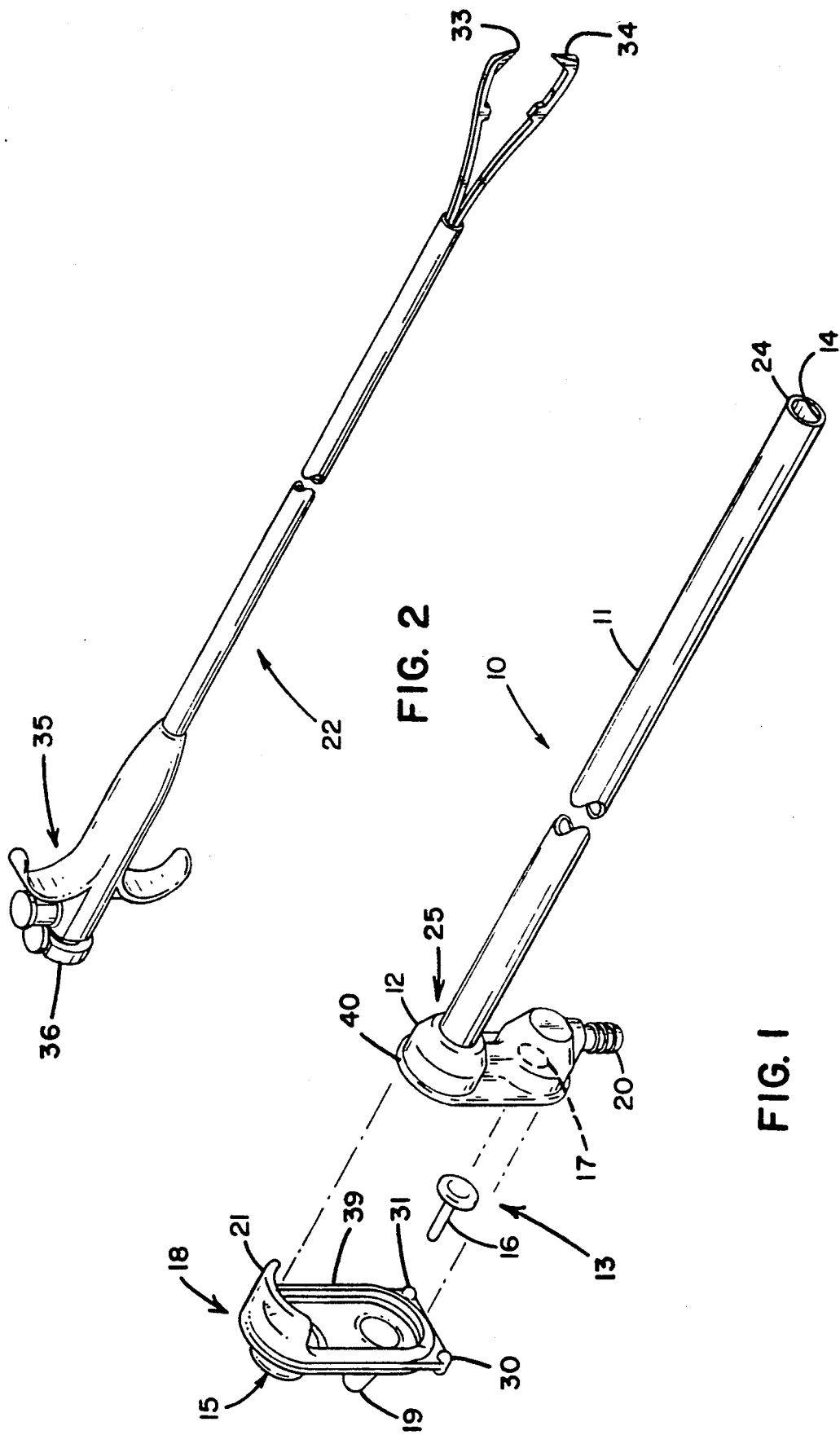

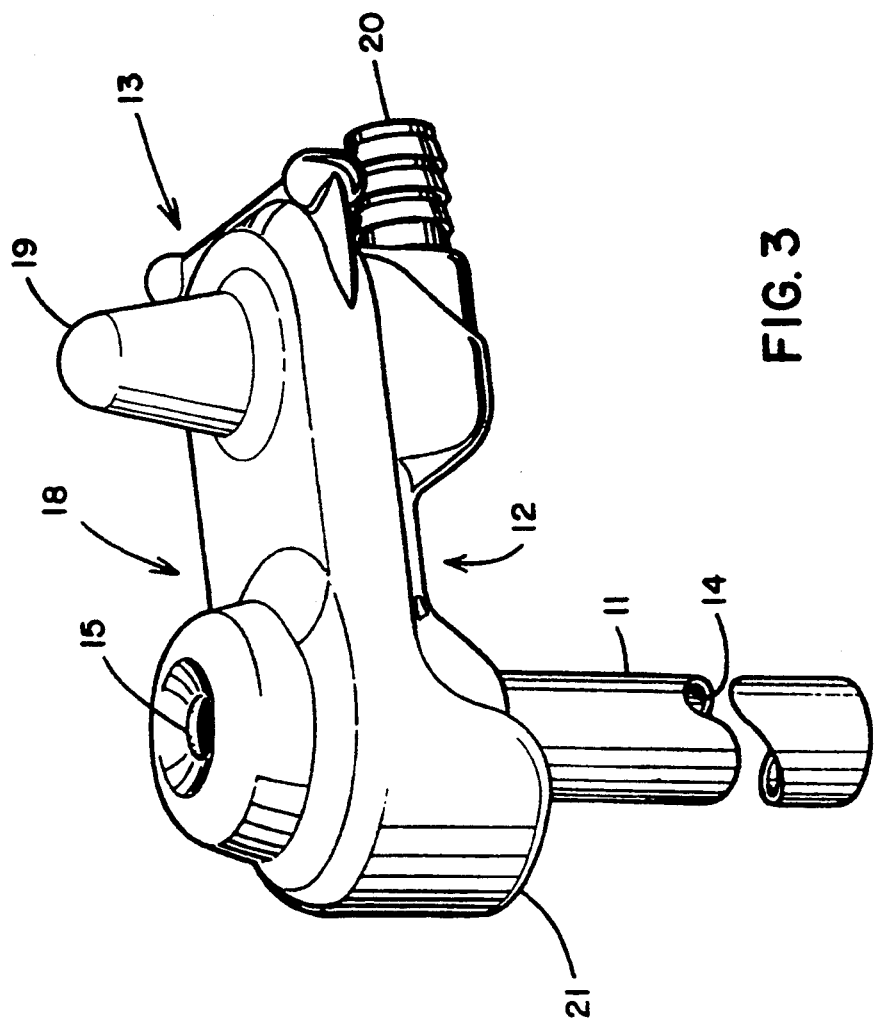

ENDOSCOPIC ASPIRATOR SURGICAL INSTRUMENT

BACKGROUND OF THE INVENTION

1. Field of the Invention

The present invention relates to surgical instruments for use during laparoscopic surgery. More particularly, the invention is an aspirator instrument for use inside the abdominal cavity for clearing the surgical field of irrigating fluid, blood and other materials.

2. Description of the Prior Art

The typical laparoscopic surgical procedure begins with the puncture of the patient's abdominal wall and the placement of an access port. Next, the abdominal cavity is partially inflated with gas, forming a pneumoperitoneum. A laparoscope or endoscope is then inserted through the access port to permit viewing of the organs during the surgical procedure. Typically the laparoscope has both an eyepiece and a video monitor so that the surgeon may see the surgical field. Additional access ports may be placed elsewhere on the abdominal wall to permit insertion of surgical instruments into the operating field. Access ports come in a variety of diameters, and 5, 7 and 11 millimeter ports are widely used for surgery within the abdominal cavity.

During laparoscopic surgery it is important to be able to rapidly clear the surgical field of blood, clots surgical debris and irrigating fluid. Failure to maintain a clear surgical field in the presence of bleeding can require that the laparoscopic approach be abandoned in favor of more invasive traditional surgical techniques.

Several instrument for aspiration have been developed. See for example Topel et al. U.S. Pat. No. 4,958,621 which shows an aspiration instrument which includes a concentric piercing instrument. Another aspiration device commonly used during laparoscopic surgery is the Nezhat-Dorsey Suction-Irrigation device. This device includes a long tube for insertion into the body having a number of small apertures located at the distal tip. A pair of trumpet valves are coupled to the lumen of the tube. One trumpet valve admits irrigation fluid, while the other trumpet valve applies suction to the lumen. In use the surgeon can select suction or irrigation by depressing the appropriate trumpet valve. The small distal apertures limit the size of the debris which can be removed with the device. Experience has shown that this prior art device can become easily clogged limiting its usefulness.

BRIEF SUMMARY OF THE INVENTION

The endoscopic sponge aspirator includes a relatively large diameter aspiration tube which is mounted in a handle structure. The handle structure incorporates a valve to control the application of vacuum to the aspiration tube. The handle structure also includes an elastic cover which can be readily removed intraoperatively to clear the instrument without removing the aspiration tube from the operating field. The elastic cover includes a tool access port which permits insertion of a grasping tool into the aspiration tube.

The grasping tool is an integral part of the system. The grasping tool takes up some of the volume of the aspiration tube and improves aspiration efficiency. The grasping tool can be used to position a gauze sponge or the like at the distal end of the tube. Without a gauze sponge in the instrument the large aperture of the aspiration tube can be used to quickly aspirate large quantities of irrigation fluid or the like. With a gauze sponge occluding and extending from the distal tip of the aspiration tube vacuum applied to the aspiration tube results in the application of suction through the gauze sponge. In this configuration, the gauze prevents organs or the like from entering the aspiration tube and blocking it, while permitting the removal of fluids.

When the gauze sponge itself becomes clogged with fibrin and clotted blood the sponge may be retracted completely into the aspiration tube and the instrument removed from the surgical field where the sponge may be quickly exchanged for another sponge. The texture of the gauze sponge provides traction to permit manipulation of organs and therefore is useful for gentle blunt dissection.

BRIEF DESCRIPTION OF THE DRAWING

Throughout the several figures of the drawing like reference numerals are used to identify identical structures, wherein:

FIG. 1 is an exploded perspective view of the endoscopic sponge aspirator surgical instrument;

FIG. 2 is a perspective view of a grasping instrument suitable for use with the endoscopic sponge aspirator surgical instrument;

FIG. 3 is a perspective view of the handle of the endoscopic sponge aspirator;

DETAILED DESCRIPTION

Figure 4:
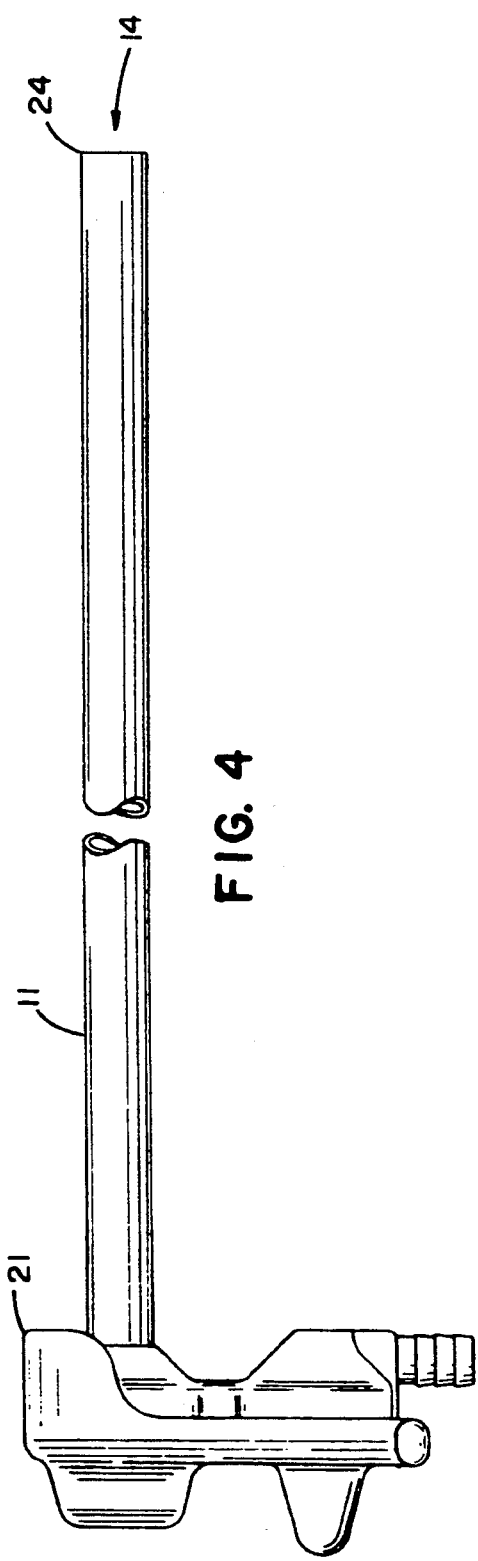
FIG. 4 is a side view of the endoscopic sponge aspirator surgical instrument.

FIG. 1 is an exploded perspective view of the endoscopic aspirator surgical instrument 10. The aspiration tube 11 has a distal tip 24, a central lumen 14 and a proximal end 25. The proximal end 25 is coupled to a plastic handle structure 12. This handle structure 12 includes a valve assembly 13, which consists of tilting valve 16; a complimentary valve seat 17 formed in the handle structure 12; and a valve cover 19. An aspiration coupler 20 is also formed integrally with the handle 12, and forms part of the valve assembly 13.

An elastic handle cover 18 is provided to cover the handle structure 12. The elastic handle cover 18 includes several molded features including the valve cover 19; a finger tab 21 and a pair of grasping nubs 30 and 31; and a tool access port 15. With the elastic handle cover 18 in place on the handle 12 the tool access port 15 is substantially concentric with the aspiration tube 11. The molded valve cover 19 positions the tilting valve 16 on its valve seat 17 and also permits the surgeon to operate the tilting valve 16, by pressing the cover 19.

Figure 5:
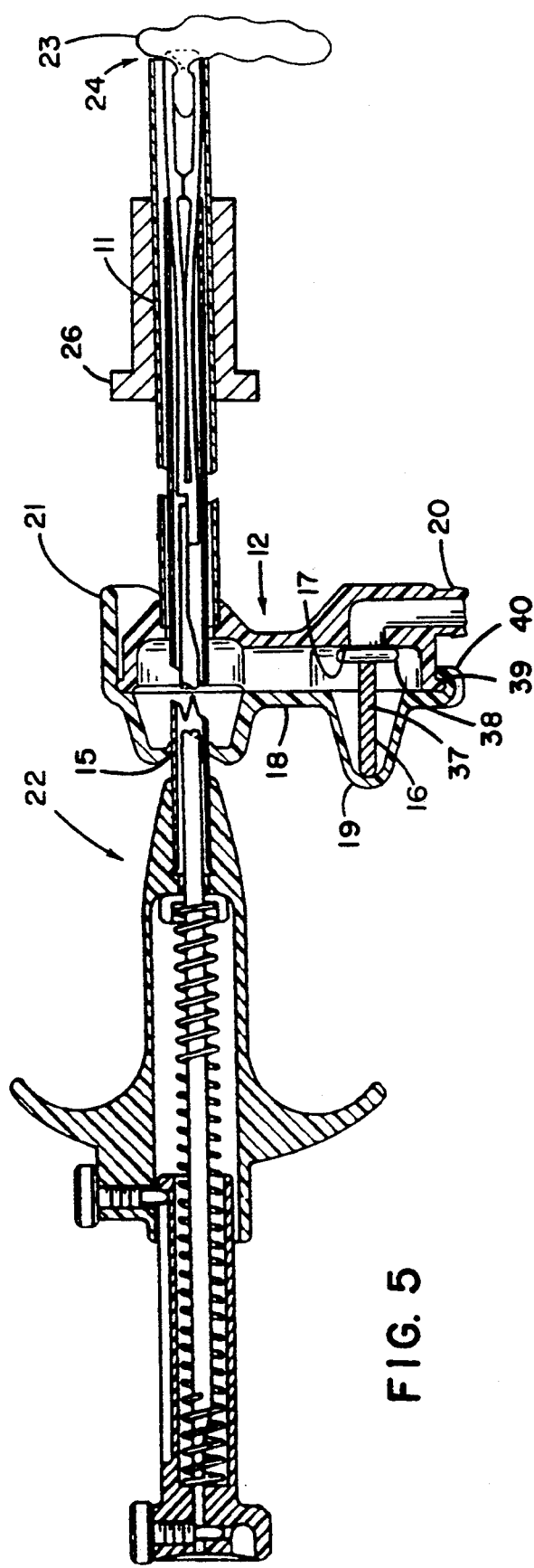
FIG. 5 is a cross-section view of the grasping tool positioned within the endoscopic sponge aspirator.

In use the surgeon can grasp the finger tab 21 or the grasping nubs 30 and 31 and readily remove the elastic cover 18 by unseating the peripheral lip 40 from the peripheral bead 39 formed on the handle 12 as best seen in FIG. 5, without moving the aspiration tube 11 from the operating field. Consequently the surgeon may quickly remove obstructions from the aspirator instrument 10 and the valve assembly 13 intraoperatively.

FIG. 2 is a perspective view of an endoscopic tenaculum grasping instrument 22 suitable for use with the endoscopic aspirator instrument 10. In use, the surgeon will insert the grasping tool 22 through the tool access port 15 to combine the grasping tool 22 with the aspirator instrument 10. The grasping tool 22 includes an operating handle 35 which allows the surgeon to open the jaws 33 and 34 by squeezing the pommel 36 into the operating handle 35. Although the endoscopic tenaculum is the preferred grasping tool 22 for use with the aspirator instrument 10, other laparoscopic grasping tools may be substituted without departing from the scope of the invention.

FIG. 3 is a perspective view of the aspirator instrument 10 showing the proximal handle 12 covered by the elastic handle cover 18. This drawing shows the tool access port 15 which receives the grasping tool 22. The substantially conical valve cover 19 formed in the elastic handle cover 18 permits the surgeon to operate the tilting valve assembly 13 with the same hand that manipulates the grasping tool 22. The aspiration coupler 20 connects the valve assembly 13 and the lumen 14 of the aspiration tube 11 to a remote vacuum source (not shown). The valve cover positions the valve stem over the valve seat 17 so that the valve disk 38 seals against the valve seat 17 unless operated by the surgeon as best seen in FIG. 5.

FIG. 4 is a side view of the endoscopic sponge aspirator surgical instrument 10 with the grasping tool removed showing the general layout of the aspirator instrument 10. Typically the length of the aspiration tube 11 is approximately 30 cm and has a diameter of approximately 11 mm to seal well with an 11 mm port. The preferred grasping tool has a diameter of approximately 5 mm. The volume of the grasping tool within the lumen 14 of the aspiration tube 11 improves the aspiration performance of the aspirator instrument 10.

It is preferred to form the entire aspirator instrument 10 form plastic and to use it as a disposable product. Preferably polypropylene products are used for the aspiration tube 11 and a co-polyester such as Hytrel (DuPont) for the handle 12. The preferred material for the elastomeric cover is Kraton thermoplastic rubber (Shell Chemical Company). Other materials and dimensions may be substituted without departing from the scope of the invention.

FIG. 5 is a cross-section view of endoscopic aspirator instrument 10 with the grasping tool 22 inserted through the tool access port 15. This drawing depicts the surgical gauze sponge 23 positioned at the distal tip 14 of the aspirator tube 11. In use, the surgeon will load the gauze sponge 23 into the aspiration tube before inserting the instrument 10 into the abdominal access port. In this connection one should note that with the tenaculum instrument 22 fully inserted into the aspirator instrument 10 the jaws 33 and 34 can be extended beyond the distal tip 24 to capture the sponge 23. However with the jaws 33 and 34 in their fully retracted position the jaws lie completely within the aspiration tube 11.

Once configured, the sponge 23 is firmly held in the distal tip 24 where it completely occludes the lumen of the aspiration tube 11 and typically extends beyond the distal end of the tube. In this position a swabbing motion is readily applied by the surgeon, and the gauze sponge may be used to manipulate organs.

Figure 6:
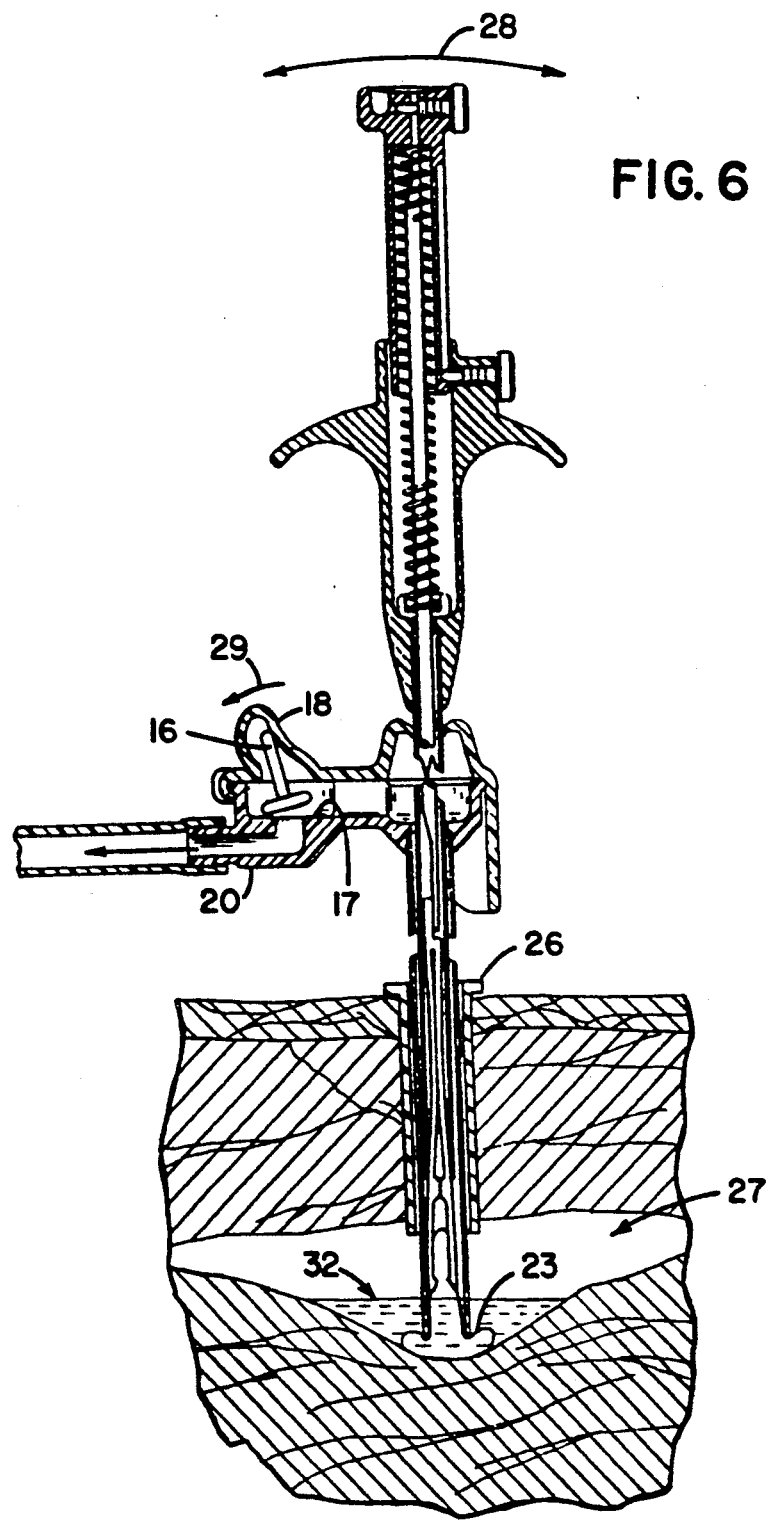
FIG. 6 is a cross-section view of the grasping tool positioned within the endoscopic sponge aspirator in use within a body cavity illustrating the sponge within the operating field.

FIG. 6 is a cross-section view of the grasping tool 22 positioned within the endoscopic aspirator instrument 10 and the assembly in use within a body cavity. In this figure the gauze sponge 23 is positioned within the operating field 27. Gentle motion of the grasping tool 22 along the path 28 permits the surgeon to manipulate and position the gauze sponge 23 within the operating field 27. When the surgeon presses the valve cover 19 the valve 16 moves off the valve seat 17, which permits the evacuation of fluid and debris through the aspiration coupler 20.

Figure 7:
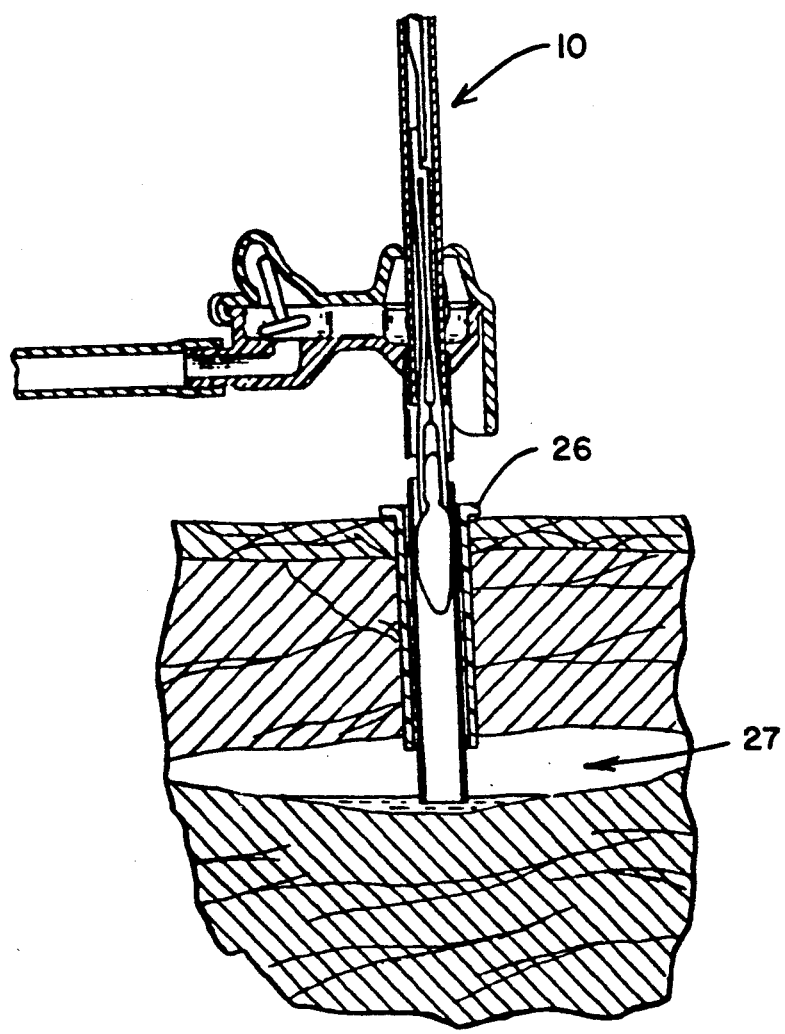
FIG. 7 is a cross-section view of the grasping tool positioned within the endoscopic sponge aspirator in use within a body cavity illustrating the sponge being cleared within the aspirator tube.

FIG. 7 shows the instrument in use with the gauze sponge completely retracted into the aspiration tube 11. In this position the entire instrument can be removed from the abdominal access port 26 and withdrawn from the surgical field 27. In this fashion the sponge can be removed, exchanged and rapidly returned to service.

What is claimed is:

1. An endoscopic aspirator instrument for use with a grasping instrument said grasping instrument having a first diameter, said aspirator instrument comprising:

a substantially straight aspiration tube having a central axis said aspiration tube having a continuous circular cross-section, a distal tip, a proximal end, and a single lumen, said lumen having a circular cross-section and having a second diameter;

a handle coupled to said proximal end of said aspiration tube;

aspiration valve assembly means proximate said handle for connecting said lumen to a source of vacuum, and for regulating the application of vacuum to said lumen;

cover means coupled to said handle;

tool access port means having a size substantially equal to said first diameter, located proximate said cover means substantially concentric with said central axis for admitting said grasping instrument to said lumen;

said grasping instrument and said lumen together defining an aspiration volume having a cross sectional area substantially equal to the difference between said first diameter and said second diameter.

2. The instrument of claim 1 wherein said aspiration valve assembly means comprises:

a tilting valve stem and a valve disk;

a valve seat located in said handle proximate said valve disk;

a valve cover for positioning said valve stem to locate said valve disk on said valve seat;

whereby said tilting valve is maintained on said valve seat by said valve cover and vacuum supplied to said valve seat.

3. The instrument of claim 1 wherein said cover means comprises:

a unitary elastomeric cover having a peripheral lip for mating engagement with a peripheral bead formed on said handle.

4. The instrument of claim 3 wherein said elastomeric cover includes a finger tab for facilitating removal of said peripheral lip from said peripheral bead.

5. An endoscopic aspirator instrument for use with a grasping instrument and a surgical sponge, said grasping instrument having a first diameter, said surgical sponge having a sponge volume, said aspirator instrument comprising:

an aspiration tube having a central axis, a distal tip, said distal tip having a central distal tip opening, a proximal end, and a lumen, said lumen having a continuous circular cross-section and having a second diameter, said central distal tip having a diameter equal to said second diameter;

a handle coupled to said proximal end of said aspiration tube;

aspiration valve assembly means proximate said handle for connecting said lumen to a source of vacuum, and for regulating the application of vacuum to said lumen;

cover means coupled to said handle;

tool access port means having a size substantially equal to said first diameter, located proximate said cover means substantially concentric with said central axis for admitting said grasping instrument to said lumen;

whereby said grasping instrument may move axially along said axis to retract said surgical sponge into said lumen defining a first position for said sponge and, whereby said grasping instrument may move axially along said axis to advance said surgical sponge out of said distal tip opening defining a second position for said sponge;

said grasping instrument and said lumen together defining an aspiration area having a cross sectional area value substantially equal to the difference between said first diameter and said second diameter;

whereby said sponge may be cleansed in said second position by aspiration through said aspiration area.

* * * * *

UNITED STATES PATENT AND TRADEMARK OFFICE
CERTIFICATE OF CORRECTION

PATENT NO. : 5,310,406
DATED : May 10, 1994
INVENTOR(S) : Sharpe, et al

Page 1 of 2

It is certified that error appears in the above-indentified patent and that said Letters Patent is hereby corrected as shown below:

In column 1, line 28 please remove the comma "," between the word "blood" and "clots"

In column 1, line 33, please delete the word "instrument" and insert therefor -- instruments--

In column 1, lines 34 and 35, please delete "Topel et al. U.S. Pat. No. 4,958,621" and insert therefor --U.S. Patent 4,958,621 to Topel et al.--

In column 3, line 43, please delete the word "form" and insert therefor --from--

UNITED STATES PATENT AND TRADEMARK OFFICE
CERTIFICATE OF CORRECTION

PATENT NO. : 5,310,406

DATED : May 10, 1994

INVENTOR(S) : Sharpe et al

It is certified that error appears in the above-indentified patent and that said Letters Patent is hereby corrected as shown below:

In column 4, lines 42 and 43, please delete the words "cross sectional" and insert therefor --cross-sectional--

In column 4, line 48, after the word "valve", please insert --having a valve--

In column 6, line 12, please delete the words "cross sectional" and insert therefor --cross-sectional--

Signed and Sealed this

Eighth Day of November, 1994

Attest:

BRUCE LEHMAN

*Attesting Officer*     *Commissioner of Patents and Trademarks*